United States Patent [19]

Campbell et al.

[11] 3,947,381

[45] Mar. 30, 1976

[54] METHOD OF MAKING A CATALYST

[75] Inventors: John Stewart Campbell; Phineas Davies; John Russell Richmond, all of Stockton-on-Tees, England

[73] Assignee: Imperial Chemical Industries Limited, London, England

[22] Filed: Dec. 17, 1973

[21] Appl. No.: 425,281

Related U.S. Application Data

[63] Continuation of Ser. No. 182,147, Sept. 20, 1971, abandoned.

[30] Foreign Application Priority Data

Oct. 8, 1970 United Kingdom............... 47914/70

[52] U.S. Cl. ...... 252/466 B; 252/466 J; 252/466 PT
[51] Int. Cl.² ...................... B01J 23/40; B01J 23/74
[58] Field of Search ....... 252/466 J, 466 PT, 466 B; 48/197 R

[56] References Cited

UNITED STATES PATENTS

| 3,186,797 | 6/1965 | Pearce et al. ................... 252/457 X |
| 3,549,556 | 12/1970 | Dienes ............................. 252/466 J |
| 3,600,145 | 8/1971 | Johnson et al. ................... 48/197 R |

*Primary Examiner*—W. J. Shine
*Attorney, Agent, or Firm*—Cushman, Darby & Cushman

[57] ABSTRACT

A catalyst comprising a metal from Group VIII of the Periodic Table, a hydraulic binding agent and alumina in the form of sheets of fine crystallites is suitable for the removal, by methanation, of carbon oxides from hydrogen-containing gases or of hydrogen from synthetic methane.

2 Claims, No Drawings

METHOD OF MAKING A CATALYST

This is a continuation of Ser. No. 182,147, filed Sept. 20, 1971, now abandoned.

This invention relates to a catalyst especially suitable for removal, by methanation, of small concentrations of carbon oxides or of hydrogen present in gas mixtures.

The manufacture of hydrogen is extensively carried out by reacting a hydrocarbon or other carbonaceous material with steam or oxygen or both. The first product of such a reaction is a mixture of carbon oxides and hydrogen; then the carbon monoxide is converted to carbon dioxide by reaction with steam and the carbon dioxide is removed, usually by absorption in an alkaline liquor such as an ethanolamine solution or a mixture containing potassium carbonate. Alternatively cryogenic separation of carbon dioxide can be used. If the carbon monoxide is itself a desired product it can be removed and subsequently recovered by means of a cuprammonium solution. All these methods leave a small concentration, usually under 2% of carbon oxides, in the gas. These are poisonous to ammonia synthesis catalysts and to certain hydrogenation catalysts based on platinum-group metals or on cobalt/molybdenum. It has become customary to render them innocuous by converting them catalytically to methane by the reactions $$CO + 3H_2 \rightarrow CH_4 + H_2O$$

$$CO_2 + 4H_2 \rightarrow CH_4 + 2H_2O$$

which proceed almost to completion if the temperature is low enough. A technical problem arises, however, in finding a catalyst for this reaction which has sufficient activity at the rather low temperatures at which it is to be used, which maintains its activity for long periods, and which nevertheless does not use a high concentration of expensive ingredients such as nickel and chromium, per unit of reactor volume.

A like problem arises during the manufacture of natural gas substitutes by reacting higher hydrocarbons with steam. The product of this reaction may contain hydrogen as an impurity, which is undesirable since it increases the flame-speed of the gas and also decreases its calorific value. This hydrogen can be converted into methane by reactions similar to those shown above, and a suitable catalyst is required. Carbon monoxide can be removed in the same way.

The invention provides a catalyst suitable for the reaction of carbon dioxide or carbon monoxide or both with hydrogen, which comprises a metal from Group VIII of the Periodic Table, a hydraulic binding agent and alumina in the form of sheets of fine crystallites.

The invention includes catalysts suitable for methanation of carbon monoxide and carbon dioxide or of carbon monoxide without reaction of carbon dioxide.

The Group VIII metal can be nickel or cobalt or can be a platinum group metal, for example ruthenium. The catalyst may contain a compound of a metal from Group VIA of the Periodic Table but this is unnecessary and not preferred, owing to the expense incurred. The concentration of nickel or cobalt is preferably in the range 10–50%, for example 15–30%, calculated as equivalent NiO on the oxide-form precursor of the catalyst as described below. If a platinum-group metal is used, its concentration is suitably in the range 0.1 to 5%, especially 0.2 to 1%.

It will be understood that catalysts for reduction reactions are normally prepared by first making an oxide-form precursor, which is suitable for handling in manufacture and commerce, but which has to be reduced by means of e.g. hydrogen at 200°–400°C to give an active catalyst. Hence it is convenient to define the composition of the catalyst in terms of the constituents, such as NiO, present at the oxide stage. In this specification the proportions of ingredients, unless otherwise indicated, are calculated in relation to the oxide composition free of materials (e.g. water and carbon dioxide) volatile at 900°C.

The hydraulic binding agent is preferably of the Portland Cement type or a low silica aluminous cement as sold under the name "Ciment Fondu", "Secar" or "Alcoa". The cement suitably makes up 20–80% of the total catalyst in oxide form.

The alumina in the form of sheets of fine crystallites is an important constituent of the catalyst since it permits the catalyst to have high porosity, low density and high mechanical strength. The alumina structure appears to be maintained to a substantial extent in the precursor composition and the catalyst, despite the physical and chemical treatments to which it is subjected. It is preferred that all the alumina present (other than any added as cement) should be in the sheet form or in forms resulting from transformation of it recurring in the preparation of the precursor or catalyst. Other aluminas can be present, however, if desired, and/or other catalyst support oxides, such as from Group IIA, for example magnesia. The proportion of sheet-type alumina is preferably at least 10% and preferably 30–70%.

The alumina appears to be a poorly crystalline "bohmite" (which may be referred to as a pseudo-bohmite) having possibly some loosely bound water. The thickness of the alumina sheets is very suitably of the order of 20–30 Angstrom units. The length of the crystallites in the plane of the sheets appears to be very suitably up to 60 Angstrom units. It is not necessary for the crystallites in the sheets to be perfectly aligned; and indeed good results are obtained using alumina sheets which are considerably "crumpled" in both dimensions of the sheet. These data as to the structure of the alumina are based chiefly on electron microscopy and on X-ray diffraction (line broadening) measurements.

The alumina can be made by double decomposition of an aluminium salt with an alkali metal precipitant such as sodium hydroxide or carbonate or aluminate, or of an alkali metal aluminate with an acid, suitably carbonic acid. The precipitate should be in the form of flocculated fine particles; gel-producing conditions should be avoided. Alternatively in ammonia or ammonium carbonate precipitant may be reacted with an aluminium salt. At the end of the precipitation there should preferably be an excess of alkali, up to 3 pH units. The precipitate is preferably aged at 50°–100° for 0.25–5 hours and, in any event, should be washed substantially free of electrolytes. It can be dried but is preferably not dehydrated or heated above 350°C before being used in making the catalyst composition.

The invention provides also a method of making the catalyst which comprises mixing together, in finely-powdered form, a Group VIII metal compound which is the oxide or is readily decomposable to the oxide, the alumina and the hydraulic binding agent, forming the mixture into catalyst shapes, treating them with liquid water or steam or both, then drying and reducing. If it is desired to make the catalyst precursor in oxide form, the reduction stage is omitted, but will, of course, later be carried out by the catalyst-user.

The method includes preferably a calcination stage, suitably at 300°–500°C, after the ingredients have been shaped. Preferably this precedes the treatment of the shapes with water or steam to cause setting of the cement.

The formation of catalyst shapes is preferably effected by dry-compression in a die; and it is found that high pressures are not needed, owing to the high pellet strength resulting from the use of the sheet-type alumina and the cement. High pressures are, moreover, not desirable since they increase the density and thus the cost of the catalyst at the oxide stage. A suitable pellet density is in the range 0.9 to 1.3.

Alternative methods such as dry-compaction between rollers can also be used for shaping the material or for preparing the material for dry-compression.

The invention provides a process of methanation in which a gas mixture containing hydrogen and at least one carbon oxide is passed over a catalyst as defined herein at a temperature and pressure appropriate for methanation. The process is especially useful when the gas is a hydrogenation gas or synthesis gas. Typically the concentration of carbon oxides is less than 2%, especially less than 1%. Typically in a hydrogenation gas or synthesis gas the hydrogen concentration is at least 50%. Important gases to be treated by methanation include hydrogen-methane mixtures in which the methane content is up to about 8%: these are valuable in hydrogenation, hydro-treating and hydro-cracking processes. Another important gas is ammonia synthesis gas, which before methanation contains about 20% $N_2$, 60–70% $H_2$ and fractional percentages of methane and noble gases, in addition to carbon oxides.

If the gas to be treated is a synthetic natural gas, its starting hydrogen content can be, for example, in the range 0.5 to 20%, and carbon dioxide can be present. Thus the catalyst according to the invention can be used in penultimate stages or the final stage of a process for making synthetic natural gas from a liquid hydrocarbon by reaction with steam.

The temperature is suitably in the range 200°C to 500°C preferably 250°–350°C. In order to control the temperature, measures such as recycle of cooled reacted gas or indirect heat exchange in the catalyst bed or multi-stage operation with intermediate cooling may be adopted.

The pressure is suitably up to 250 atmospheres or more, for example at ammonia synthesis pressure, and can be 5–40 atmospheres as in synthesis gas or hydrogenation gas as produced by steam reforming or partial oxidation.

The catalyst should be protected from poisons, such as sulphur in a concentration over about 0.2 ppm and especially over about 1 ppm, if long term operation at high activity is required.

EXAMPLE 1

Catalyst precursor preparation

An aqueous solution of nickel nitrate hexahydrate (2500 ml) containing 7.97 g. of NiO per 100 ml was reacted with a molar solution of sodium carbonate to give an excess alkalinity of 5.37 g of $Na_2CO_3/100$ ml.

The precipitate of basic nickel carbonate which resulted was washed thoroughly, dried at 120°C and calcined at 350°C for 6 hours to convert it substantially to nickel oxide. The oxide (105.3 g) was ground finely and mixed dry with sheet-type alumina of bulk density 0.27 g/cc (252 g), also finely powdered, 149.3 g of the low-silica aluminous cement sold under the Registered Trade Mark "Ciment Fondu" 16.0 g of light magnesia and 10.3 g of powdered graphite. The mixture was compressed into cylindrical pellets 5.4 mm in diameter by 3.6 mm high. The pellets were calcined overnight at 400°C, allowed to cool, soaked in water for 24 hours and dried at 120°C. Their pellet density was now 1.13 g/cc, corresponding to a bulk density of 0.77. The weight percentage composition of the catalyst precursor on a loss free basis was:

| | |
|---|---|
| NiO | 25.2 |
| $Al_2O_3$ | 50.0 |
| $SiO_2$ | 2.1 |
| CaO | 13.1 |
| MgO | 2.2 |
| $Fe_2O_3$ | 5.9 |

Test of Catalyst

The catalyst was tested in comparison with an equal volume of commercially available methanation catalyst containing (before reduction) 25% of NiO together with magnesia, gamma alumina and hydraulic cement and having a bulk density of 1.03. Each catalyst precursor was reduced from the oxide-form to active catalyst by means of a crude ammonia synthesis gas simulating that made by steam reforming, shift and $CO_2$ - removal, that is, containing about 69% of hydrogen and about 23% nitrogen, together with methane, noble gases, 0.3% % of and 0.2% $CO_2$, at 285°C (inlet temperature), a pressure of 30 atm. absolute and a space velocity of 10,000$^{hr-1}$. These conditions were maintained after reduction and the outlet CO and $CO_2$ contents were measured. It was found that the total outlet carbon oxide content was 0.014% for both catalysts, and that this performance was maintained for 600 hours. Thus the catalyst according to the invention is as effective as the commercial catalyst, despite the lower weight of it which was required.

EXAMPLE 2

A sample of a new batch of the catalyst described in Example 1 was tested in a run simulating the final methanation stage of a process for making synthetic natural gas starting with steam and a liquid hydrocarbon feedstock. The inlet gas was passed at a space velocity of 4750 liters per liter of catalyst-filled space per hour over the catalyst at an inlet temperature of 248°C and a pressure of 225 psig (17 kg/cm² absolute). The Table shows that hydrogen was removed down to a level (1.3%, equivalent to about 1.7% after removal of the carbon dioxide) at which it would have little effect on the flame speed of the gas.

TABLE

| | | $CO_2$ | CO | $CH_4$ | $H_2$ | $N_2$ |
|---|---|---|---|---|---|---|
| Gas Composition* | Inlet | 21.7 | 0.9 | 72.0 | 5.2 | 0.2 |
| % v/v | Outlet | 22.1 | 0.19 | 76.2 | 1.3 | 0.21 |

*These values relate to the dry gas constituents, the inlet gas also contained 6.0 parts by volume of steam to each 100 volumes of dry gas.

I claim:

1. A method of making a catalyst which comprises mixing together, in finely-powdered form, a Group VIII metal oxide, a hydraulic binding agent, forming the mixture into compressed pellets having a pellet density in the range of 0.9 to 1.3, treating said pellets with water or steam or both, then drying and reducing with a reducing agent at 200°–400°C.

2. A method according to claim 1 in which the mixture is calcined at 300°–500°C after forming said pellets.

* * * * *